(12) United States Patent
Farrukh Hamza

(10) Patent No.: US 11,549,930 B2
(45) Date of Patent: Jan. 10, 2023

(54) MEASURING MECHANICAL PROPERTIES OF ROCK CUTTINGS

(71) Applicant: Halliburton Energy Services, Inc., Houston, TX (US)

(72) Inventor: Syed Muhummad Farrukh Hamza, Tomball, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 457 days.

(21) Appl. No.: 16/756,104

(22) PCT Filed: Dec. 11, 2017

(86) PCT No.: PCT/US2017/065651
§ 371 (c)(1),
(2) Date: Apr. 14, 2020

(87) PCT Pub. No.: WO2019/117857
PCT Pub. Date: Jun. 20, 2019

(65) Prior Publication Data
US 2020/0326322 A1    Oct. 15, 2020

(51) Int. Cl.
G06K 9/00     (2022.01)
B06B 3/00     (2006.01)
G01N 33/24    (2006.01)
G01B 21/20    (2006.01)
G01G 19/52    (2006.01)
G01M 7/02     (2006.01)
G06K 9/62     (2022.01)
G06V 10/56    (2022.01)

(52) U.S. Cl.
CPC ............. *G01N 33/24* (2013.01); *G01B 21/20* (2013.01); *G01G 19/52* (2013.01); *G01M 7/025* (2013.01); *G06K 9/6289* (2013.01); *G06V 10/56* (2022.01)

(58) Field of Classification Search
CPC .................................. G06K 9/00; B06B 3/00
USPC ....... 382/100, 103, 106, 108, 121, 162, 168, 382/173, 181, 199, 203, 193, 220, 224, 382/254, 274, 276, 285–291, 305, 318; 166/250.11; 703/2; 299/39.4; 175/206; 210/85; 73/32, 663, 662
See application file for complete search history.

(56) References Cited

U.S. PATENT DOCUMENTS

| | | | |
|---|---|---|---|
| 4,809,791 A * | 3/1989 | Hayatdavoudi | E21B 44/00 175/206 |
| 9,249,654 B2 * | 2/2016 | Strachan | E21B 44/00 |
| 2011/0094950 A1 * | 4/2011 | Dahl | B07B 1/4618 210/85 |

(Continued)

*Primary Examiner* — Seyed H Azarian
(74) *Attorney, Agent, or Firm* — Kilpatrick Townsend & Stockton LLP

(57) ABSTRACT

A system for measuring mechanical properties of rock cuttings includes a vibration platform with an upper surface configured to vibrate a plurality of rock cuttings thereon. A sensor system is operatively connected to the vibration platform to monitor the rock cuttings vibrating on the upper surface of the vibration platform. A calculation module is operatively connected to the vibration platform and the sensor system to calculate mechanical properties of the rock cuttings based on applied vibrational force frequency of the vibration platform and measurements of the rock cuttings from the sensor system.

18 Claims, 1 Drawing Sheet

(56) References Cited

U.S. PATENT DOCUMENTS

| | | | | |
|---|---|---|---|---|
| 2012/0130693 A1* | 5/2012 | Ertas | ............ | E21B 44/00 |
| | | | | 703/2 |
| 2014/0225417 A1* | 8/2014 | Meinders | ............ | E02F 9/0858 |
| | | | | 299/39.4 |
| 2015/0020588 A1* | 1/2015 | Larson | ............ | G01N 9/00 |
| | | | | 73/32 R |
| 2016/0177709 A1* | 6/2016 | Li | ............ | E21B 28/00 |
| | | | | 166/250.11 |

* cited by examiner

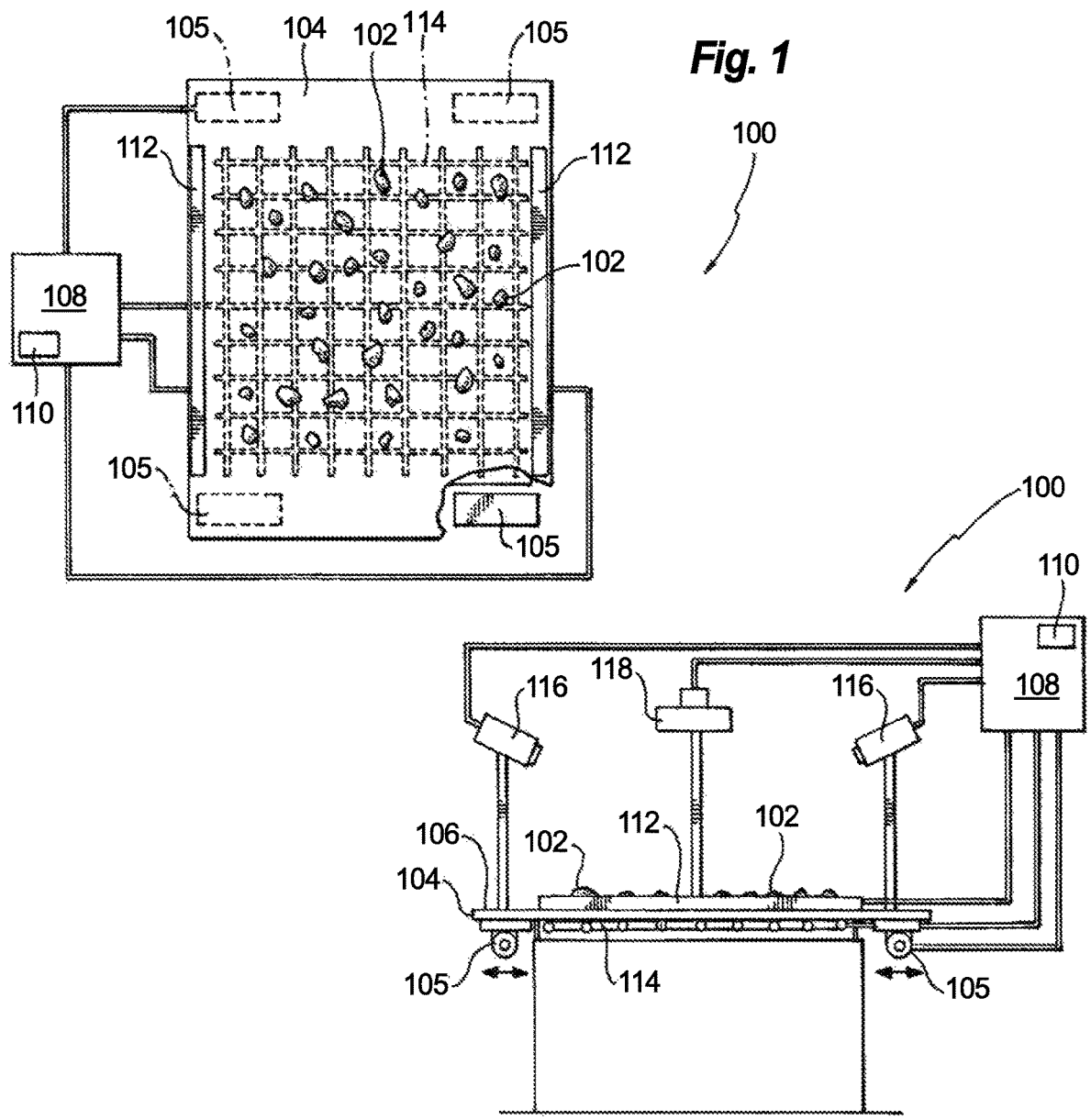
*Fig. 1*
*Fig. 2*
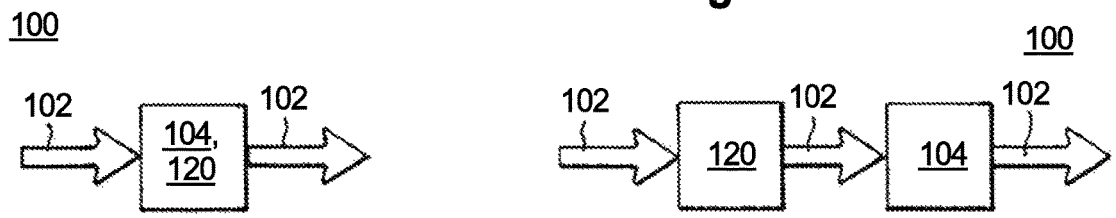
*Fig. 3*
*Fig. 4*

MEASURING MECHANICAL PROPERTIES OF ROCK CUTTINGS

BACKGROUND OF THE INVENTION

1. Field of the Invention

The present disclosure relates to measurements, and more particularly to measuring mechanical properties of rock cuttings, e.g., from drilling operations.

2. Description of Related Art

In drilling operations, e.g., where earth formations are drilled to obtain hydrocarbon gas and liquid, rock cuttings are conveyed to the surface from the drilling equipment. The rock cuttings can provide valuable information about the formations being drilled.

In order to gain information from the rock cuttings, the mechanical properties of the rock cuttings must be determined. When they reach the surface, the rock cuttings are separated from drilling fluids on a shale shaker, also referred to as a shaker table. A technician selects rock cuttings from the shaker table. Any remaining mud and drilling fluid is removed, and a given rock cutting must be shaped into a standard test sample geometry. Once it is shaped into standard sample geometry, the rock cutting sample can be subjected to standard mechanical tests to determine its mechanical properties. The mechanical properties of the rock cuttings can inform decisions needed for the drilling operation.

The conventional techniques have been considered satisfactory for their intended purpose. However, there is an ever present need for improved measurement of rock cuttings. This disclosure provides a solution for this need.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein:

FIG. 1 is a schematic plan view of an exemplary embodiment of a system constructed in accordance with the present disclosure, showing rock cuttings being measured on a vibration platform;

FIG. 2 is a schematic side elevation view of the system of FIG. 1, showing imaging sensors for imaging the rock cuttings;

FIG. 3 is a schematic view of the system of FIG. 1 in which the vibration platform is part of a shale shaker; and FIG. 4 is a schematic view of the system of FIG. 1 in which the vibration platform is separate from and downstream of a shale shaker.

DETAILED DESCRIPTION OF THE PREFERRED EMBODIMENTS

Reference will now be made to the drawings wherein like reference numerals identify similar structural features or aspects of the subject disclosure. For purposes of explanation and illustration, and not limitation, a partial view of an exemplary embodiment of a system in accordance with the disclosure is shown in FIG. 1 and is designated generally by reference character 100. Other embodiments of systems in accordance with the disclosure, or aspects thereof, are provided in FIGS. 2-4, as will be described. The systems and methods described herein can be used for automated measurement of mechanical properties of rock cuttings.

The system 100 makes automated measurements of mechanical properties, e.g., geomechanical properties, of rock cuttings 102. The rock cuttings 102 are of various shapes and sizes, and for the sake of clarity not all of the rock cuttings 102 are labeled with a reference character in FIGS. 1-2. The system 100 includes a vibration platform 104 with an upper surface 106, which is labeled in FIG. 2, configured to vibrate the plurality of rock cuttings 102 thereon. Actuators 105 drive vibration platform 104 and causing vibration of the rock cuttings 102 on the upper surface 106 thereof.

A sensor system 108 is operatively connected to the vibration platform 104 to monitor the rock cuttings 102 vibrating on the upper surface 102 of the vibration platform 104. The sensor system is connected to the actuators 105 to monitor the force frequency applied to the vibration platform 104. A calculation module 110 is operatively connected to the vibration platform 104 and to the sensor system 108 to calculate mechanical properties of the rock cuttings 102 based on applied vibrational force frequency of the vibration platform 104 and measurements of the rock cuttings 102 from the sensor system 108.

The calculation module 110 is operatively connected to the sensor system 108, e.g., as part of a single computer device, software module, or as different computer devices or software modules networked together in a common network, to monitor measured displacement of the rock cuttings 102, dimensions of the rock cuttings 102, applied vibrational force frequency and/or weight of the rock cuttings 102. The sensor system 108 includes one or more sensors 112 for measuring displacement for each rock cutting and including at least one of proximity sensors, laser distance sensors, contact accelerometers, and/or non-contact microphone sensors. The sensor system 108 also includes a grid 114 of load cells mounted to the vibration platform 104, e.g. within the vibration platform 104 or on a surface of the vibration platform 104 opposite the upper surface 106, to measure weight of the rock cuttings 102. As shown in FIG. 2, the sensor system 108 includes one or more imaging sensors 116 operatively connected to the vibration platform 104 to measure surface color, shape and dimensions of the rock cuttings 102. The imaging sensors 116 are connected to provide image data to the sensor system 108 and can include cameras positioned to have a field of view covering a suitable amount of the upper surface 106 of the vibration platform 104 to obtain images of the rock cuttings 102. The images can provide size and shape data, as well as data on the surface color, for the rock cuttings 102. The sensor system 108 includes a 3-d surface scanner 118 operatively connected to the vibration platform 104 to measure three-dimensional shape, including the size, of the rock cuttings 102.

The calculation module 110 includes machine readable instructions to cause the calculation module to receive input from the sensor system 108 including at least one of vibrational force frequency and amplitude, measured displacement of the rock cuttings, dimensions and/or weight of the rock cuttings from the sensors described above. The machine readable instructions also cause the calculation module to calculate, based on the input from the sensor system, at least one geomechanical property of the rock cuttings including at least one of dynamic Young's modulus, shear modulus, and/or Poisson's ratio. These properties can be output provided to a user, e.g., on a display or as a printout, and can be used to update a database of rock cuttings' metrics to improve subsequent measurements of rock cuttings, e.g., by machine learning and/or direct mapping, and to provide formation data for ongoing and future drilling operations. With respect to direct mapping, as an example, for each type of formation lithology, a number of rock cuttings can be tested in a lab, either on-site or off-site, using conventional mechanical testing methods such as impulse hammer method, brittleness testing methods, hardness measurements, uniaxial testing, triaxial testing, and the like. The results from the testing can be used to calibrate, correct and/or correlate with the automated shale table measurements.

To account for mud which may cling to the rock cuttings 102, the calculation module 110 can include machine readable instructions to cause the calculation module to receive image data from at least one image sensor 116, use an image recognition algorithm on the image data to determine quantity of mud sticking to a rock cutting 102, use mud weight data to calculate weight of the quantity of mud, subtract the weight of the quantity of mud from weight of the rock cutting to which the mud is sticking, and calculate, based on the input from the sensor system 108 corrected to subtract mud weight, at least one geomechanical property of the rock cuttings 102 including at least one of dynamic Young's modulus, shear modulus, and/or Poisson's ratio.

With reference now to FIG. 3, the system 100 can include a shale shaker 120, wherein the vibration platform 104 is a vibration platform of the shale shaker 120. For example, the sensor system 108 can monitor rock cuttings 102 on part or all of a vibration platform of the shale shaker 120. The sensors described above can be installed as a retrofit on an existing shale shaker 120, for example. It is also contemplated that system 100 can include a shale shaker 120, wherein the vibration platform 104 is a separate component installed downstream of the shale shaker 120, as shown in FIG. 4, to receive the rock cuttings 102 from the shale shaker 120 that are separated from drilling fluid by the shale shaker. There are advantages to having calculation module 110 on site with the vibration platform 104, however those skilled in the art having had the benefit of this disclosure will readily appreciate that the calculation module can be off-site from the vibration platform 104 without departing from the scope of this disclosure.

A method of measuring mechanical properties of rock cuttings includes using a sensor system, e.g. the sensor system 108, and a vibration platform, e.g., the vibration platform 104, to measure response of the rock cuttings to vibration to measure mechanical properties of rock cuttings directly without re-shaping the rock cuttings. Measuring mechanical properties of rock cuttings includes automated calculation of mechanical properties based on applied vibrational force frequency of the vibration platform and measurements of the rock cuttings from the sensor system. Automated calculation of mechanical properties includes monitoring with the sensor system at least one of measured displacement of the rock cuttings, dimensions of the rock cuttings, and/or weight of the rock cuttings. Automated calculation of mechanical properties can include monitoring surface color of the rock cuttings with the sensor system, and using surface color in automated calculation of mechanical properties. Automated calculation of mechanical properties can include monitoring three-dimensional shape of the rock cuttings with the sensor system, and using three-dimensional shape of the rock cuttings in automated calculation of mechanical properties. Automated calculation of mechanical properties can include calculating, based on input from the sensor system, at least one geomechanical property of the rock cuttings including at least one of dynamic Young's modulus, shear modulus, and/or Poisson's ratio. The method can include using at least one of machine learning and direct mapping to correlate mechanical properties of the rock cuttings to at least one of measured displacement of the rock cuttings, dimensions of the rock cuttings, weight of the rock cuttings, surface color of the rock cuttings, and/or three-dimensional shape of the rock cuttings.

Sensor system 108 can provide all parameters needed for calculation of dynamic mechanical properties of the rock cuttings 102. The calculation described in ASTM E-1876, which is a standard test method for dynamic Young's modulus, shear modulus, and Poisson's ratio by impulse excitation of vibration, can be used in calculation module 110 to calculate the mechanical properties. A custom computation method can also be used in lieu of or in addition to ASTM E-1876. The ASTM E-1876 test method measures the fundamental resonant frequency of test specimens of suitable geometry by exciting them mechanically. The appropriate fundamental resonant frequencies, dimensions, and mass of the specimen are used to calculate dynamic Young's modulus, dynamic shear modulus, and Poisson's ratio.

Data output from calculation module 110, including mechanical properties of the rock cuttings 102, can be plotted against depth for various subsurface lithologies and rock strata. This provides a useful comparison for acoustic log data, which is also used to measure dynamic mechanical properties.

The number of rock cuttings 102 can be determined and the characteristics of the rock cuttings 102 can be determined in an automated manner. Analytical, numerical, or empirical techniques can be applied, using measured data, to determine dynamic measurement properties. ASTM standards, or any other suitable standards, can be applied and corrections, such as for mud clinging to the rock cuttings 102, can be made to make the standards applicable. The standards can be adapted to apply to odd-shaped samples in a quantitative manner, e.g., corrections can be made for certain factors including size, shape, and lithology of the rock cuttings so that the ASTM standards can be applied to the rock cuttings. It is also contemplated that in a qualitative manner, mechanical properties can be determined on a grading scale, e.g., where a formation is graded for a given mechanical property on a scale of 1-5. It is also contemplated that a system such as the system 100 can be calibrated empirically, e.g., using actual cuttings in impact static force tests and/or a 3-d scanner database to calculate mechanical properties of the rock cuttings 102. It is also contemplated that numerical techniques can be used to calculate mechanical properties from image data, 3-d scanner data, or other sensor data characterizing the rock cuttings 102.

Those skilled in the art having had the benefit of this disclosure will readily appreciate that multiple types of sensors are disclosed herein as part of the sensor system 108, and that each sensor provides respective advantages, but that it is possible to omit one or more of the sensors and still obtain meaningful measurements with remaining sensors without departing from the scope of this disclosure.

Systems and methods as disclosed herein can provide additional quantitative mud logging capability at the wellsite during drilling operations compared to traditional techniques. Real-time measurement of rock cuttings' dynamic mechanical properties at the wellsite can now be accomplished while drilling takes place. The measured dynamic rock properties can be compared with subsurface sonic log data.

Output from systems and methods as disclosed herein can be useful in a variety of actions either at the wellsite or in an off-site setting such as evaluation of wellbore stability, prediction of drill bit life, fracture design, prediction of penetration of perforation shaped charges, design of mud weight window for safe drilling, sanding potential prediction, and any other suitable application of mechanical properties of rock cuttings. A drilling operation can be adjusted in real time based on the actions above. For example, if the mechanical properties of the rock cuttings 102 indicate a formation being drilled will lead to shortened drill bit life, the drill bit can be steered to avoid the formation to the greatest extent possible to preserve drill bit life. A fracture design can be executed based on the mechanical properties of the rock cuttings. Big data applications from automated measurement of rock cuttings can expand and/or improve known correlations related to earth formations.

Accordingly, as set forth above, the embodiments disclosed herein may be implemented in a number of ways. For example, in general, in one aspect, the disclosed embodiments relate to a system for measuring mechanical properties of rock cuttings. The system includes a vibration platform with an upper surface configured to vibrate a plurality of rock cuttings thereon. A sensor system is operatively connected to the vibration platform to monitor the rock cuttings vibrating on the upper surface of the vibration platform. A calculation module is operatively connected to the vibration platform and the sensor system to calculate mechanical properties of the rock cuttings based on applied vibrational force frequency of the vibration platform and measurements of the rock cuttings from the sensor system.

In general, in another aspect, the disclosed embodiments relate to a method of measuring mechanical properties of rock cuttings. The method includes using a sensor system and a vibration platform to measure response of the rock cuttings to vibration to measure mechanical properties of rock cuttings directly without re-shaping the rock cuttings.

In accordance with any of the foregoing embodiments, the calculation module can be operatively connected to the sensor system to monitor at least one of measured displacement of the rock cuttings, dimensions of the rock cuttings, applied vibrational force frequency and/or weight of the rock cuttings.

In accordance with any of the foregoing embodiments the sensor system can include one or more sensors for measuring displacement for each rock cutting and including at least one of proximity sensors, laser distance sensors, contact accelerometers, and/or non-contact microphone sensors.

In accordance with any of the foregoing embodiments, the sensor system can include a grid of load cells mounted to the vibration platform to measure weight of the rock cuttings.

In accordance with any of the foregoing embodiments, the sensor system can include one or more imaging sensors operatively connected to the vibration platform to measure surface color of the rock cuttings.

In accordance with any of the foregoing embodiments, the sensor system can include a 3-d surface scanner operatively connected to the vibration platform to measure three-dimensional shape of the rock cuttings.

In accordance with any of the foregoing embodiments, the calculation module can include machine readable instructions to cause the calculation module to receive input from the sensor system including at least one of vibrational force frequency, measured displacement of the rock cuttings, dimensions and/or weight of the rock cuttings; and calculate, based on the input from the sensor system, at least one geomechanical property of the rock cuttings including at least one of dynamic Young's modulus, shear modulus, and/or Poisson's ratio.

In accordance with any of the foregoing embodiments, the sensor system can include at least one image sensor, wherein the calculation module includes machine readable instructions to cause the calculation module to: receive image data from the at least one image sensor; use an image recognition algorithm on the image data to determine quantity of mud sticking to a rock cutting; use mud weight data to calculate weight of the quantity of mud; subtract the weight of the quantity of mud from weight of the rock cutting to which the mud is sticking; and calculate, based on the input from the sensor system corrected to subtract mud weight, at least one geomechanical property of the rock cuttings including at least one of dynamic Young's modulus, shear modulus, and/or Poisson's ratio.

In accordance with any of the foregoing embodiments, a shale shaker can be included, wherein the vibration platform is a vibration platform of the shale shaker and/or the vibration platform can be a separate component installed downstream of the shale shaker to receive the rock cuttings from the shale shaker that are separated from drilling fluid by the shale shaker.

In accordance with any of the foregoing embodiments, the calculation module can be on site with the vibration platform, and/or the calculation module can be off-site from the vibration platform.

In accordance with any of the foregoing embodiments, measuring mechanical properties of rock cuttings can include automated calculation of mechanical properties based on applied vibrational force frequency of the vibration platform and measurements of the rock cuttings from the sensor system.

In accordance with any of the foregoing embodiments, automated calculation of mechanical properties can include monitoring with the sensor system at least one of measured displacement of the rock cuttings, dimensions of the rock cuttings, and/or weight of the rock cuttings.

In accordance with any of the foregoing embodiments, automated calculation of mechanical properties can include monitoring surface color of the rock cuttings with the sensor system, and using surface color in automated calculation of mechanical properties.

In accordance with any of the foregoing embodiments, automated calculation of mechanical properties can include monitoring three-dimensional shape of the rock cuttings with the sensor system, and using three-dimensional shape of the rock cuttings in automated calculation of mechanical properties.

In accordance with any of the foregoing embodiments, automated calculation of mechanical properties can include calculating, based on input from the sensor system, at least one geomechanical property of the rock cuttings including at least one of dynamic Young's modulus, shear modulus, and/or Poisson's ratio.

In accordance with any of the foregoing embodiments, the method can include receiving image data from the at least one image sensor of the sensor system; using an automated image recognition algorithm on the image data to determine quantity of mud sticking to a rock cutting; using mud weight data to calculate weight of the mud; subtracting the weight of the mud from weight of the rock cutting to which the mud is sticking; and calculating, based on the input from the sensor system corrected to subtract mud weight, at least one geomechanical property of the rock cuttings including at least one of dynamic Young's modulus, shear modulus, and/or Poisson's ratio.

In accordance with any of the foregoing embodiments, the method can include using at least one of machine learning and direct mapping to correlate mechanical properties of the rock cuttings to at least one of measured displacement of the rock cuttings, dimensions of the rock cuttings, weight of the rock cuttings, surface color of the rock cuttings, and/or three-dimensional shape of the rock cuttings.

In accordance with any of the foregoing embodiments, measuring mechanical properties can include using analytical, numerical, and/or empirical techniques with measured data to determine the mechanical properties.

In accordance with any of the foregoing embodiments, measuring mechanical properties can include making corrections so a standard can be applied to calculate the mechanical properties of the ruck cuttings, wherein the corrections include corrections to at least one of size, shape, and/or lithology of the rock cuttings.

In accordance with any of the foregoing embodiments, measuring mechanical properties can include determining the mechanical properties on a qualitative grading scale.

The methods and systems of the present disclosure, as described above and shown in the drawings, provide for measurement of mechanical properties of rock cuttings with superior properties including automated measurement of a variety of sizes and shapes of rock cuttings in real time. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A system for measuring mechanical properties of rock cuttings comprising: a vibration platform with an upper surface configured to vibrate a plurality of rock cuttings thereon;
a sensor system operatively connected to the vibration platform to monitor the rock cuttings vibrating on the upper surface of the vibration platform, wherein the sensor system comprises one or more imaging sensors operatively connected to the vibration platform to measure surface color of the rock cuttings; and
a calculation module operatively connected to the vibration platform and the sensor system to calculate mechanical properties of the rock cuttings based on applied vibrational force frequency of the vibration platform and measurements of the rock cuttings from the sensor system, wherein the calculation module comprises machine readable instructions to cause the calculation module to:
receive input from the sensor system including at least one of vibrational force frequency, measured displacement of the rock cuttings, dimensions of the rock cuttings, or weight of the rock cuttings; and
calculate, based on the input from the sensor system, at least one geomechanical property of the rock cuttings including at least one of dynamic Young's modulus, shear modulus, or Poisson's ratio.

2. The system as recited in claim 1, wherein the calculation module is operatively connected to the sensor system to monitor at least one of measured displacement of the rock cuttings, dimensions of the rock cuttings, applied vibrational force frequency and/or weight of the rock cuttings.

3. The system as recited in claim 1, wherein the sensor system includes one or more sensors for measuring displacement for each rock cutting and including at least one of proximity sensors, laser distance sensors, contact accelerometers, and/or non-contact microphone sensors.

4. The system as recited in claim 1, wherein the sensor system includes a grid of load cells mounted to the vibration platform to measure weight of the rock cuttings.

5. The system as recited in claim 1, wherein the sensor system includes a 3-d surface scanner operatively connected to the vibration platform to measure three-dimensional shape of the rock cuttings.

6. The system as recited in claim 1, wherein the sensor system includes at least one image sensor, wherein the calculation module includes machine readable instructions to cause the calculation module to:
receive image data from the at least one image sensor;
use an image recognition algorithm on the image data to determine quantity of mud sticking to a rock cutting;
use mud weight data to calculate weight of the quantity of mud;
subtract the weight of the quantity of mud from weight of the rock cutting to which the mud is sticking; and
calculate, based on the input from the sensor system corrected to subtract mud weight, at least one geomechanical property of the rock cuttings including at least one of dynamic Young's modulus, shear modulus, and/or Poisson's ratio.

7. The system as recited in claim 1, further comprising a shale shaker, wherein the vibration platform is a vibration platform of the shale shaker.

8. The system as recited in claim 1, further comprising a shale shaker, wherein the vibration platform is a separate component installed downstream of the shale shaker to receive the rock cuttings from the shale shaker that are separated from drilling fluid by the shale shaker.

9. The system as recited in claim 1, wherein the calculation module is on site with the vibration platform.

10. The system as recited in claim 1, wherein the calculation module is off-site from the vibration platform.

11. A method of measuring mechanical properties of rock cuttings comprising:
using a sensor system and a vibration platform to measure response of the rock cuttings to vibration to measure mechanical properties of rock cuttings directly without re-shaping the rock cuttings, wherein measuring the mechanical properties of the rock cuttings includes automated calculation of the mechanical properties based on applied vibrational force frequency of the vibration platform and measurements of the rock cuttings from the sensor system, wherein the automated calculation of the mechanical properties includes monitoring surface color of the rock cuttings with the sensor system and using the surface color in the automated calculation of the mechanical properties, and wherein the automated calculation of the mechanical properties includes calculating, based on input from the sensor system, at least one geomechanical property of the rock cuttings including at least one of dynamic Young's modulus, shear modulus, or Poisson's ratio.

12. The method as recited in claim 11, wherein automated calculation of mechanical properties includes monitoring with the sensor system at least one of measured displacement of the rock cuttings, dimensions of the rock cuttings, and/or weight of the rock cuttings.

13. The method as recited in claim 11, wherein automated calculation of mechanical properties includes monitoring three-dimensional shape of the rock cuttings with the sensor system, and using three-dimensional shape of the rock cuttings in automated calculation of mechanical properties.

14. The method as recited in claim 11, further comprising:
receiving image data from at least one image sensor of the sensor system;
using an automated image recognition algorithm on the image data to determine quantity of mud sticking to a rock cutting;
using mud weight data to calculate weight of the mud;
subtracting the weight of the mud from weight of the rock cutting to which the mud is sticking; and
calculating, based on the input from the sensor system corrected to subtract mud weight, at least one geomechanical property of the rock cuttings including at least one of dynamic Young's modulus, shear modulus, and/or Poisson's ratio.

15. The method as recited in claim 11, further comprising using at least one of machine learning and direct mapping to correlate mechanical properties of the rock cuttings to at least one of measured displacement of the rock cuttings, dimensions of the rock cuttings, weight of the rock cuttings, surface color of the rock cuttings, and/or three-dimensional shape of the rock cuttings.

16. The method as recited in claim 11, wherein measuring mechanical properties includes using analytical, numerical, and/or empirical techniques with measured data to determine the mechanical properties.

17. The method as recited in claim 11, wherein measuring mechanical properties includes making corrections so a standard can be applied to calculate the mechanical properties of the rock cuttings, wherein the corrections include corrections to at least one of size, shape, and/or lithology of the rock cuttings.

18. The method as recited in claim 11, wherein measuring mechanical properties includes determining the mechanical properties on a qualitative grading scale.

* * * * *